United States Patent [19]

Oswald et al.

[11] 4,104,378

[45] Aug. 1, 1978

[54] COMBATTING PESTS WITH O,S-DIALKYL-O-(4-PHENYLAZOPHENYL)-THIOPHOSPHATES

[75] Inventors: Alexis A. Oswald, Mountainside; Paul L. Valint, Woodbridge, both of N.J.

[73] Assignee: Ciba-Geigy Corporation, Ardsley, N.Y.

[21] Appl. No.: 816,559

[22] Filed: Jul. 18, 1977

Related U.S. Application Data

[60] Division of Ser. No. 666,120, Mar. 11, 1976, Pat. No. 4,051,240, which is a continuation-in-part of Ser. No. 377,855, Jul. 9, 1973, abandoned.

[30] Foreign Application Priority Data

Jul. 7, 1972 [CH] Switzerland .................... 10210/72
May 11, 1973 [CH] Switzerland .................... 6720/73

[51] Int. Cl.² .......................... A01N 9/00; A01N 9/36
[52] U.S. Cl. ................................. 424/225; 424/211
[58] Field of Search ............................... 424/225, 211

[56] References Cited

U.S. PATENT DOCUMENTS

| | | | |
|---|---|---|---|
| 2,183,998 | 12/1939 | McNally et al. | 260/206 X |
| 2,200,543 | 5/1940 | Dickey et al. | 260/205 |
| 2,234,704 | 3/1941 | McNally et al. | 260/205 |
| 2,328,570 | 9/1943 | McNally et al. | 260/196 X |
| 2,947,663 | 8/1960 | Losco et al. | 260/260 X |
| 3,825,632 | 7/1974 | Pallos | 260/944 |
| 3,826,830 | 7/1974 | Pallos | 260/944 X |

*Primary Examiner*—Allen J. Robinson
*Attorney, Agent, or Firm*—Frederick H. Rabin

[57] ABSTRACT

Organophosphorus acid esters of the formula

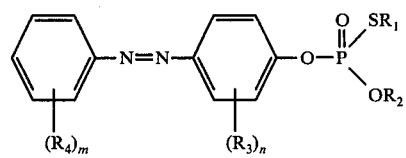

wherein $R_1$ represents propyl or butyl; $R_2$ represents methyl or ethyl; each of $R_3$ and $R_4$ represents hydrogen, halogen, or alkyl having 1 to 5 carbon atoms; $n$ is a number from 1 to 4; and $m$ is a number from 1 to 5. These compounds are useful for the control of insects, acarids and nematodes.

9 Claims, No Drawings

COMBATTING PESTS WITH O,S-DIALKYL-O-(4-PHENYLAZOPHENYL)-THIO-PHOSPHATES

CROSS-REFERENCE TO RELATED APPLICATION

This is a division of application Ser. No. 666,120 filed on Mar. 11, 1976, now U.S. Pat. No 4,051,240, which is a continuation-in-part of application Ser. No. 377,855 filed on Jul. 9, 1973, now abandoned.

The present invention relates to new organophosphorus acid esters, to pesticidal compositions containing them, and to their use for controlling pests, particularly insects, acarids and nematodes.

The compounds have the formula

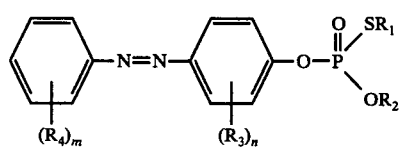

wherein $R_1$ represents propyl or butyl; $R_2$ represents methyl or ethyl; each or $R_3$ and $R_4$ represents hydrogen, halogen, or alkyl having from 1 to 5 carbon atoms; $n$ is a number from 1 to 4; and $m$ is a number from 1 to 5.

By halogen is meant fluorine, chlorine, bromine, or iodine, but especially chlorine or bromine.

The alkyl groups $R_3$ and $R_4$ can be a straight-chain or branched. Examples of such groups include: methyl, ethyl, n-propyl, isopropyl, n-butyl, isobutyl, sec.butyl, tert.butyl, n-pentyl and isomers thereof. The alkyl group $R_1$ can be any $C_3$ or $C_4$ alkyl, straight-chain or branched.

Of particular interest are compounds of formula I in which $R_1$ is propyl or butyl; $R_2$ is methyl or ethyl; each of $R_3$ and $R_4$ is hydrogen, chlorine or methyl; $n$ is 1; and $m$ is 1 or 2.

Preferred are compounds of formula I in which $R_1$ is n-propyl, isopropyl or isobutyl.

According to a more preferred embodiment of this invention, the compounds have the formula

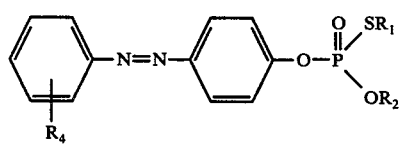

in which $R_1$ is n-propyl or isobutyl; $R_2$ is methyl or ethyl; and $R_4$ is hydrogen, chlorine or methyl in the 2- or 4-position. Especially preferred are compounds of formula II in which $R_1$ is n-propyl, $R_2$ is ethyl and $R_4$ is in the 4-position.

The compounds of formula I are manufactured by the following known methods:

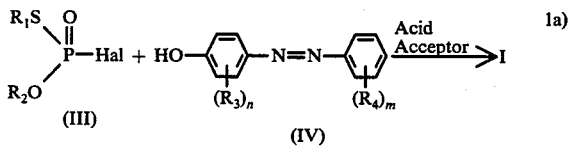

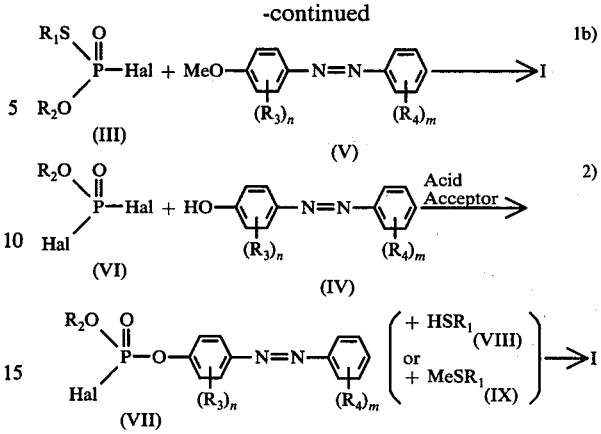

In the formulae III to IX, $R_1$, $R_2$, $R_3$, $R_4$, $n$ and $m$ have the meanings given for the formula I. Hal represents a halogen atom, in particular chlorine. Me represents an alkali metal, especially sodium or potassium, an ammonium or alkylammonium group.

Suitable acid acceptors are: tertiary amines, e.g. trialkylamine, pyridine, dialkyl anilines; inorganic bases, e.g. hydrides, hydroxides; carbonates and bicarbonates or alkali metals and alkaline earth metals. It is sometimes necessary to use catalysts in the reactions, for example copper or copper chloride. Processes 1a, 1b, and 2 are carried out at a reaction temperature between $-2°$ C and $130°$ C, at normal pressure, and in solvents or diluents.

Examples of suitable solvents or diluents are: ether and ethereal compounds, e.g. diethyl ether, dipropyl ether, dioxan, tetrahydrofuran; amides, e.g. N,N-dialkylated carboxylic acid amides; aliphatic, aromatic, and halogenated hydrocarbons, in particular benzene, toluene, xylene, chloroform, chlorobenzene; nitriles, e.g. acetonitrile; dimethyl sulphoxide; ketones, e.g. acetone, methyl ethyl ketone; and water.

The starting materials of the formulae III, IV, V, VI, VIII and IX can be manufactured in analogous manner to known methods.

The compounds of formula I have a broad biocidal activity spectrum and can therefore be used for combatting various plant and animal pests. In particular, they are suitable for combatting insects, acarids, and nematodes. Insects combatted include the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudoccidae, Chrysomolidae, Coccinellidae, Bruchidae, Scarabaeidae, Dermestidae, Tenebrionidae, Curcurionidae, Tineidae, Noctuidae, Lymantriidae, Pyralidae, Galleriidae, Culicidae, Tipulidae, Stomoxydae, Muscidae, Calliphoridae, Trypetidae and Pulicidae. Acarids combatted include the families: Ixodidae, Argasidae, Tetranychidae and Dermanyssidae.

By addition of other insecticides and/or acaricides it is possible to improve substantially the insecticidal or acaricidal action and to adapt it to given circumstances.

In addition, the compounds of formula I also display activity against representatives of the division Thallophyta. Thus, a number of these compounds display bactericidal action. But they are active particularly against phytopathogenic fungi which belong to the following classes: Oomycetes, Zygomycetes, Ascomycetes, Basidiomycetes and Denteromycetes. The compounds of formula I also evidence a fungitoxic action against fungi which attack the plants from the soil. Further, these new compounds are also suitable for treating seeds, fruit, tubers, etc., to protect them from fungus infections. The compounds of formula I are also suitable for combatting plant pathogenic nematodes.

In U.S. Pat. No. 2,947,663, there are disclosed O,O-dialkyl-O-(4-phenylazophenyl)-phosphates and -thiophosphates of the formula

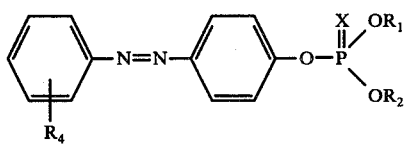

(X)

in which $R_1$ and $R_2$ represent methyl or ethyl; $R_4$ represents hydrogen, halogen, nitro, methyl, methoxy or ethoxy; and X represents oxygen or sulphur. The new compounds of formula I differ from the known compounds of formula X in that they are asymmetric "mixed" esters. Rather than having two identical alkoxy groups, the compounds of formula I have one alkoxy group and one alkylthio group. Furthermore, in these alkoxy and alkylthio groups, the alkyl moieties are different; in particular, the alkyl moiety of the alkoxy group is methyl or ethyl and the alkyl moiety of the alkylthio group is a propyl or butyl radical. The combined effect of these two differences results in compounds having superior insecticidal effectiveness and, in many cases, lower mammalian toxicity than the previously known analogues.

The compounds of formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilizers.

For application, the compounds of formula I may be processed to dusts, emulsion concentrates, granules, dispersions, sprays, solutions, or suspensions, in the conventional formulation which is commonly employed in application technology. Mention may also be made of cattle dips and spray races, in which aqueous preparations are used.

The compositions according to the invention are manufactured in known manner by intimately mixing and/or grinding active substances of formula I with the suitable carriers, optionally with the addition of dispersants or solvents which are inert towards the active substances. The active substances may take, and be used in, the following forms:

Solid forms:
  Dusts, tracking agents, granules, coated granules, impregnated granules and homogeneous granules.
Liquid forms:
  (a) active substances which are dispersible in water: wettable powders, pastes, emulsions;
  (b) solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilizers, for example ammonium sulphate, ammonium phosphate, ammonium nitrate, urea, ground vegetable products, such as corn meal, bark dust, sawdust, nutshell meal, cellulose powder, residues of plant extractions, activated charcoal, etc. These substances can either be used singly or in admixture with one another.

Granules can be very easily manufactured by dissolving an active substance of formula I in an organic solvent and applying the resulting solution to a granulated material, for example attapulgite, $SiO_2$, granicalcium, bentonite, etc., and then evaporating the solvent.

Polymer granules can also be manufactured by mixing the active substances of formula I with polymerisable compounds (urea/formaldehyde; dicyandiamide/formaldehyde; melamine/formaldehyde or others), whereupon a mild polymerization is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favorable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomizers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (Carbowax), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases, it is advantageous to use mixtures of different carriers. As dispersing agents, there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove, in such a manner that, the size of the solid particles does not exceed 0.02 to 0.04μ in wettable powders, and 0.03μ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350° C. The solvents must be practically odorless, not phytotoxic, and inert to the active substances.

Furthermore, the agents according to the invention can be applied in the form of solutions. For this purpose, the active substances, or several active substances of the general formula I, are dissolved in suitable organic solvents, mixtures of solvents or in water. Aliphatic and aromatic hydrocarbons, chlorinated derivatives thereof, alkyl naphthalenes and mineral oils, singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of formula I can, for example, be formulated as follows:

Dusts

The following substances are used to manufacture (a) a 5% and (b) a 2% dust:
(a) 5 parts of active substance
  95 parts of talcum
(b) 2 parts of active substance
  1 part of highly disperse silicic acid
  97 parts of talcum.

The active substances are mixed with the carriers and ground.

Granules

The following substances are used to produce 5% granules:
  5 parts of active substance,
  0.25 parts of epichlorohydrin,
  0.25 parts of cetyl polyglycol ether,
  3.50 parts of polyethylene glycol,
  91 parts of kaolin (particle size 0.3 - 0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder

The following consitutents are used for the preparation of (a) a 40%, (b) and (c) a 25%, and (d) a 10% wettable powder:
(a) 40 parts of active substance,
  5 parts of sodium lignin sulphonate,
  1 part of sodium dibutyl-naphthalene sulphonate,
  54 parts of silicic acid.
(b) 25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate,
  19.5 parts of silicic acid,
  19.5 parts of Champagne chalk,
  28.1 parts of kaolin.
(c) 25 parts of active substance,
  2.5 parts of isooctylphenoxy-polyoxyethylene-ethanol,
  1.7 parts of Champagne chalk/hydroxyethyl cellulose mixture (1:1),
  8.3 parts of sodium aluminum silicate,
  16.5 parts of kieselguhr,
  46 parts of kaolin.
(d) 10 parts of active substance,
  3 parts of a mixture of the sodium salts of saturated fatty alcohol sulphates,
  5 parts of naphthalenesulphonic acid/formaldehyde condensate
  82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:
  10 parts of active substance,
  3.4 parts of epoxidized vegetable oil,
  13.4 parts of a combination emulsifier consisting of fatty alcohol polyglycol ether and alkylarylsulphonate calcium salt,
  40 parts of dimethylformamide,
  43.2 parts of xylene.
(b) 25 parts of active substance,
  2.5 parts of epoxidized vegetable oil,
  10 parts of an alkylarylsulphonate/fatty alcohol-polyglycol ether mixture,
  5 parts of dimethylformamide,
  57.5 parts of xylene.

From these concentrates it is possible to produce, by dilution with water, emulsions of any desired concentration.

Spray

The following constituents are used to prepare a 5% spray:
  5 parts of active substance,
  1 parts of epichlorohydrin,
  94 parts of benzine (boiling limits 160° - 190° C).

The invention will be better understood by reference to the following examples which are included here for exemplification only and not as limitations.

Example 1

At room temperature 10.1 g of O-ethyl-S-n-propyl-thio-phosphoric chloride in 25 ml of absolute ether are added dropwise to a solution of 11.6 g of 4-hydroxy-4'-chloro-azobenzene and 5.1 g of triethylamine in 150 ml of absolute ether. The salt precipitate is filtered off and the mixture is treated with 200 ml of ice water with stirring. The organic phase is isolated, washed once with water and shaken twice with ice-cold 5% sodium hydroxide solution and then washed neutral with water. The ethereal phase is then treated with activated charcoal, filtered, dried, and the solvent is evaporated. The residue is dried for 3 hours at 70° C and 0.1 Torr to give the compound of the formula

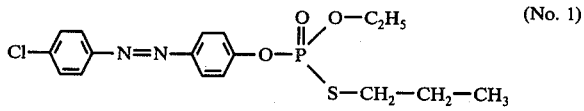
(No. 1)

with a refractive index of $n_D^{20°} = 1.6185$.

The following compounds are also manufactured in analogous manner:

| No. | Structure | Refractive Index |
|-----|-----------|------------------|
| 2 | ⌬—N=N—⌬—O—P(=O)(OC₂H₅)(SCH₂CH₂CH₃) | $n_D^{20} = 1.6142$ |
| 3 | Cl—⌬—N=N—⌬(Cl)—O—P(=O)(OC₂H₅)(SCH₂CH₂CH₃) | $n_D^{20} = 1.6251$ |
| 4 | Cl,Cl—⌬—N=N—⌬—O—P(=O)(OC₂H₅)(SCH₂CH₂CH₃) | $n_D^{20} = 1.6300$ |
| 5 | CH₃—⌬—N=N—⌬—O—P(=O)(OC₂H₅)(SCH₂CH₂CH₃) | $n_D^{20} = 1.6132$ |
| 6 | ⌬—N=N—⌬—O—P(=O)(OC₂H₅)(SCH₂—CH(CH₃)₂) | $n_D^{20} = 1.6082$ |
| 7 | Cl—⌬—N=N—⌬—O—P(=O)(OC₂H₅)(SCH₂—CH(CH₃)₂) | $n_D^{20} = 1.6078$ |
| 8 | Cl(ortho)—⌬—N=N—⌬—O—P(=O)(OC₂H₅)(SCH₂CH₂CH₃) | $n_D^{20} = 1.6018$ |

EXAMPLE 2

Action against ticks (A) *Rhipicephalus bursa*

Five adult ticks and 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardized cotton wool plug and placed on its head, so that the active substance emulsion could be adsorbed by the cotton wool.

In the case of the adults, evaluation took place after 2 weeks, and in that of the larvae, after 2 days. Each test was repeated twice.

(B) *Boophilus microplus (larvae)*

Tests were carried out in each case with 20 OP-sensitive larvae using an analogous dilution series as in the case of test A. (The OP-sensitivity refers to Diazinon).

The compounds according to Example 1 were active in these tests against adults and larvae of *Rhipicephalus bursa* sensitive and OP-resistant larvae of *Boophilus microplus*.

EXAMPLE 3

Action against *Chilo suppresalis*

Six rice plants at a time of the variety Caloro' were transplanted into plastic pots (diameter at the top — 17 cm) and reared to a height of about 60 cm. Infestation with *Chilo suppressalis* larvae (L₁: 3-4 mm long) took place 2-days after the active substance had been applied in granule form to the paddy water (rate of application: 8 kg of active substance per hectare). Evaluation of the insecticidal action took place 10 days after application of the granules.

The compounds according to Example 1 were active in the above tests against *Chilo suppressalis*.

EXAMPLE 4

Action against soil insects

Sterilized compost earth was homogenously mixed with a wettable powder containing 25% of active substance so that there resulted a rate of application of 5 kg of active substance per hectare.

Young zucchetti plants (*Cucumis pepo*) were put into plastic pots with the treated soil (3 plants per pot; diameter of pot = 7 cm). Each pot was infected immediately afterwards with 5 *Aulacophora femoralis* and Pachmoda or Chortophila larvae. The control was carried out 4, 8, 16 and 32 days after depositing the larvae.

At 80-100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

EXAMPLE 5

Acaricidal action

*Phaseoulus vulgaris* (dwarf beans) had an infested piece of leaf from a mass culture of Tetranychus urticae placed on them 12 hours before the test for the acaricidal action. The mobile stages which have migrated are sprayed with the emulsified test preparations from a chromatography atomizer so that the spray broth does not run off. The number of living and dead larvae, adults and eggs are evaluated after 2 to 7 days under a stereoscopic microscope and the result expressed in percentages. During the interim, the treated plants are kept in greenhouse compartments at 25° C.

The compounds according to Example 1 were active in the above test against eggs, larvae and adults of *Tetranychus urticae*.

EXAMPLE 6

Action against soil nematodes

To test the action against soil nematodes, the active substance is applied to and intimately mixed with soil infected with root gall nematodes (*Meloidgyne Arenaria*). Immediately afterwards, tomato cuttings are planted in the prepared soil in a series of tests and after a waiting time of 8 days, tomato seeds are sown in another test series.

In order to assess the nematocidal action, the galls present on the roots are counted 28 days after planting and sowing respectively. In this test the compounds according to Example 1 display good action against *Meloidgyne Arenaria*.

EXAMPLE 7

Comparative Insecticidal Tests

Compounds within the scope of formula II of this invention

O-ethyl-S-n-propyl-O-[4-(4'-chlorophenylazo)-phenyl]-thiophosphate — compound No. 1

O-ethyl-S-n-propyl-O-(4-phenylazophenyl)-thiophosphate — compound No. 2

O-ethyl-S-n-propyl-O-[4-(4'-methylphenylazo)-phenyl]-thiophosphate — compound No. 5 were compared with compounds of U.S. Pat. No. 2,947,663

O,O-diethyl-O-(4-phenylazophenyl)-phosphate — compound A

O,O-diethyl-O-[4-(4'-chlorophenylazo)-phenyl]-phosphate — compound B

O,O-diethyl-O-[4-(4'-methylphenylazo)-phenyl]-phosphate — compound C

O,O-diethyl-O-[4-(4'-chlorophenylazo)-phenyl]-thiophosphate — compound D

O,O-diethyl-O-[4-(4'-methylphenylazo)-phenyl]-thiophosphate — compound E in their action against *Spodoptera littoralis*.

Potato plants in the 4 to 5 leaf stage were treated by immersion in an 0.1% aqueous emulsion of the compound under test, the emulsion having been prepared from a 25% wettable powder. After drying, each plant was settled with 5 larvae of the species Spodoptera littoralis at the L-3 instar. Plastic cylinders covered with wire netting at the top were then placed over each of the plants to prevent the larvae from straying. The plants were examined after three days and the percentage of dead larvae estimated in each case. The test was conducted at 24° C and 60% relative humidity.

| Test Compound | 1 | B | D | 2 | A | 5 | C | E |
|---|---|---|---|---|---|---|---|---|
| TEST RESULTS |||||||||
| % mortality after 3 days | 100 | 0 | 0 | 100 | 0 | 100 | 0 | 0 |

Compounds numbers 1, 2 and 5, according to this invention, showed a good activity against *Spodoptera littoralis* larvae in the above test. Compounds A, B and C, according to U.S. Pat. No. 2,947,663, showed zero activity.

We claim:

1. A method for combatting insects, acarids and nematodes which comprises applying thereto an insecticidally, acaricidally or nematicidally effective amount of a compound of the formula

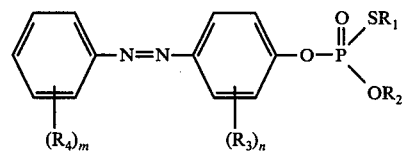

wherein $R_1$ represents propyl or butyl; $R_2$ represents methyl or ethyl; each of $R_3$ and $R_4$ represents hydrogen, halogen or alkyl having from 1 to 5 carbon atoms; $n$ is a number from 1 to 4; and $m$ is a number from 1 to 5.

2. A method according to claim 1 in which, in the compound, each of $R_3$ and $R_4$ represents hydrogen, chlorine or methyl; $n$ is 1; and $m$ is 1 or 2.

3. A method according to claim 2 in which, in the compound, $R_1$ is n-propyl or isobutyl; $R_3$ is hydrogen; $R_4$ is in the 2- or 4-position and $m$ is 1.

4. The method according to claim 3 in which the compound is O-ethyl-S-n-propyl-O-[4-(4'-chlorophenylazo)-phenyl]-thiophosphate.

5. The method according to claim 3 in which the compound is O-ethyl-S-n-propyl-O-)4-phenylazophenyl)-thiophosphate.

6. The method according to claim 2 in which the compound is O-ethyl-S-n-propyl-O-[2-chloro-4-(4'-chlorophenylazo)-phenyl]-thiophosphate.

7. The method according to claim 2 in which the compound iis O-ethyl-S-n-propyl-O-[4-(3',4'-dichlorophenylazo)-phenyl]-thiophosphate.

8. The method according to claim 3 in which the compound is O-ethyl-S-n-propyl-O-[4-(4'-methylphenylazo)-phenyl]-thiophosphate.

9. The method according to claim 2 in which the compound is O-ethyl-S-isobutyl-O-(4-phenylazophenyl)-thiophosphate.

* * * * *